United States Patent
Simpson et al.

(10) Patent No.: US 11,788,103 B2
(45) Date of Patent: Oct. 17, 2023

(54) SECONDARY ACETATE FERMENTATION

(71) Applicant: LanzaTech, Inc., Skokie, IL (US)

(72) Inventors: Sean Dennis Simpson, Skokie, IL (US); Allan Haiming Gao, Skokie, IL (US); Robert John Conrado, Skokie, IL (US); James Daniel Winkler, Skokie, IL (US); Alexander Paul Mueller, Skokie, IL (US); Steven Brown, Skokie, IL (US); Loan Phuong Tran, Skokie, IL (US); Michael Koepke, Skokie, IL (US); Christophe Daniel Mihalcea, Skokie, IL (US)

(73) Assignee: LanzaTech, Inc., Skokie, IL (US)

( * ) Notice: Subject to any disclaimer, the term of this patent is extended or adjusted under 35 U.S.C. 154(b) by 310 days.

(21) Appl. No.: 16/938,787

(22) Filed: Jul. 24, 2020

(65) Prior Publication Data
US 2021/0024961 A1    Jan. 28, 2021

Related U.S. Application Data

(60) Provisional application No. 62/878,528, filed on Jul. 25, 2019, provisional application No. 62/986,940, filed on Mar. 9, 2020.

(51) Int. Cl.
*C12P 7/04* (2006.01)
*C12P 39/00* (2006.01)

(52) U.S. Cl.
CPC ............. *C12P 7/04* (2013.01); *C12P 39/00* (2013.01)

(58) Field of Classification Search
CPC .... C12P 7/04; C12P 39/00; C12P 7/54; C12P 7/64; C12P 21/02; C12P 7/40
See application file for complete search history.

(56) References Cited

U.S. PATENT DOCUMENTS

2013/0065282 A1   3/2013  Tran et al.
2016/0122787 A1   5/2016  Simpson

FOREIGN PATENT DOCUMENTS

WO   WO 2007117157 A1 *  10/2007
WO       2008134679 A1    11/2008
WO   WO 2011088364 A2 *   7/2011
WO       2018019867 A1     2/2018

OTHER PUBLICATIONS

Whisstock et al. Quaterly Reviews of Biophysics, 2003, "Prediction of protein function from protein sequence and structure", 36(3):307-340. (Year: 2003).*
Witkowski et al. Conversion of a beta-ketoacyl synthase to a malonyl decarboxylase by replacement of the active-site cysteine with glutamine, Biochemistry. Sep. 7, 1999;38(36):11643-50. (Year: 1999).*
Kisselev L., Polypeptide release factors in prokaryotes and eukaryotes: same function, different structure. Structure, 2002, vol. 10:8-9. (Year: 2002).*
Kopke et al. 2,3-Butanediol production by acetogenic bacteria, an alternative route to chemical synthesis, using industrial waste gas. Appl and Environ Microbiol 2011, 77(15): 5467-5475). (Year: 2011).*
Yang et al. Metabolic engineering of *Escherichia coli* carrying the hybrid acetone-biosynthesis pathway for efficient acetone biosynthesis from acetate. Microb Cell Fact 2019, 18:6: p. 1-9. (Year: 2019).*
Drake, Acetogenic Prokaryotes, In: The Prokaryotes, 3rd edition, p. 354, New York, NY, 2006.
Lee, Nature Catalysis, 2: 18-33, 2019.
Ragsdale, Biochim Biophys Acta, 1784: 1873-1898, 2008.
Schiel-Bengelsdorf, FEBS Letters 586: 2191-2198, 2012.
International Search Report issued in corresponding International Application No. PCT/US2020/043417, dated Nov. 17, 2020, 3 pages.

* cited by examiner

*Primary Examiner* — Iqbal H Chowdhury

(57) ABSTRACT

The disclosure relates to the combination of a primary fermentation that converts gas to acetate with a secondary fermentation that converts acetate to a target product. Preferably, the gas contains carbon dioxide, such that the disclosure enables the fixation of carbon dioxide into useful products. The fermentations may be any combination of aerobic and anaerobic, batch and continuous. The fermenting microorganisms may typically be bacterial or fungal.

26 Claims, 2 Drawing Sheets

SECONDARY ACETATE FERMENTATION

CROSS REFERENCE

This application claims the benefit of U.S. Provisional Application Ser. No. 62/878,528 filed Jul. 25, 2019, and U.S. Provisional Application Ser. No. 62/986,940 filed Mar. 9, 2020. The content of the provisional applications is expressly incorporated herein by reference in their entirety.

FIELD

The disclosure relates to the combination of a primary fermentation that converts gas to acetate with a secondary fermentation that converts acetate to a target product. For example, the gas may contain carbon dioxide, such that the disclosure enables the fixation of carbon dioxide into useful products.

BACKGROUND

Mitigation of impending climate change requires drastic reductions in emissions of greenhouse gases (GHGs), such as those generated through the burning of fossil fuels like coal and oil. Although sustainable sources of chemicals and transportation fuels are currently insufficient to significantly displace our dependence on fossil carbon, gas fermentation has recently emerged as an alternative platform for the biological fixation of such gases such as carbon dioxide ($CO_2$), carbon monoxide (CO), and/or hydrogen ($H_2$) into sustainable fuels and chemicals. In particular, gas fermentation technology can utilize a wide range of feedstocks including gasified organic matter (for example, municipal solid waste or agricultural waste) or industrial waste gases (for example, from steel mills or oil refineries) to produce ethanol, jet fuel, and a variety of other products. Gas fermentation alone could displace 30% of crude oil use and reduce global $CO_2$ emissions by 10%, but as with any disruptive technology, many technical challenges remain before this potential is fully achieved.

SUMMARY

In one embodiment the disclosure is a method for producing at least one target product from CO and optionally $H_2$, or $CO_2$ and $H_2$. A gaseous substrate comprising at least CO and optionally $H_2$, or $CO_2$ and $H_2$ is introduced into a first bioreactor containing a culture of at least one first microorganism in a first liquid nutrient medium. The gaseous substrate is anaerobically fermented to produce acetate as a first product in a first fermentation broth. The first microorganism expresses the enzymes of the Wood-Ljungdahl pathway. At least a portion of the first fermentation broth is transferred to a second bioreactor containing a culture of at least one second microorganism in a second liquid nutrient medium. The second microorganism is a different species from the first microorganism. Fermenting the first product produces at least a first target product in a second fermentation broth.

Other embodiments and options of operation are possible. Some of these are discussed in more detail below.

BRIEF DESCRIPTION OF THE DRAWINGS

FIG. 2 shows, as another further embodiment, a water electrolyzer being used to generate at least a portion of the $H_2$ used in the primary bioreactor and at least a portion of the $O_2$ used in the secondary bioreactor.

DESCRIPTION

Figure 1:
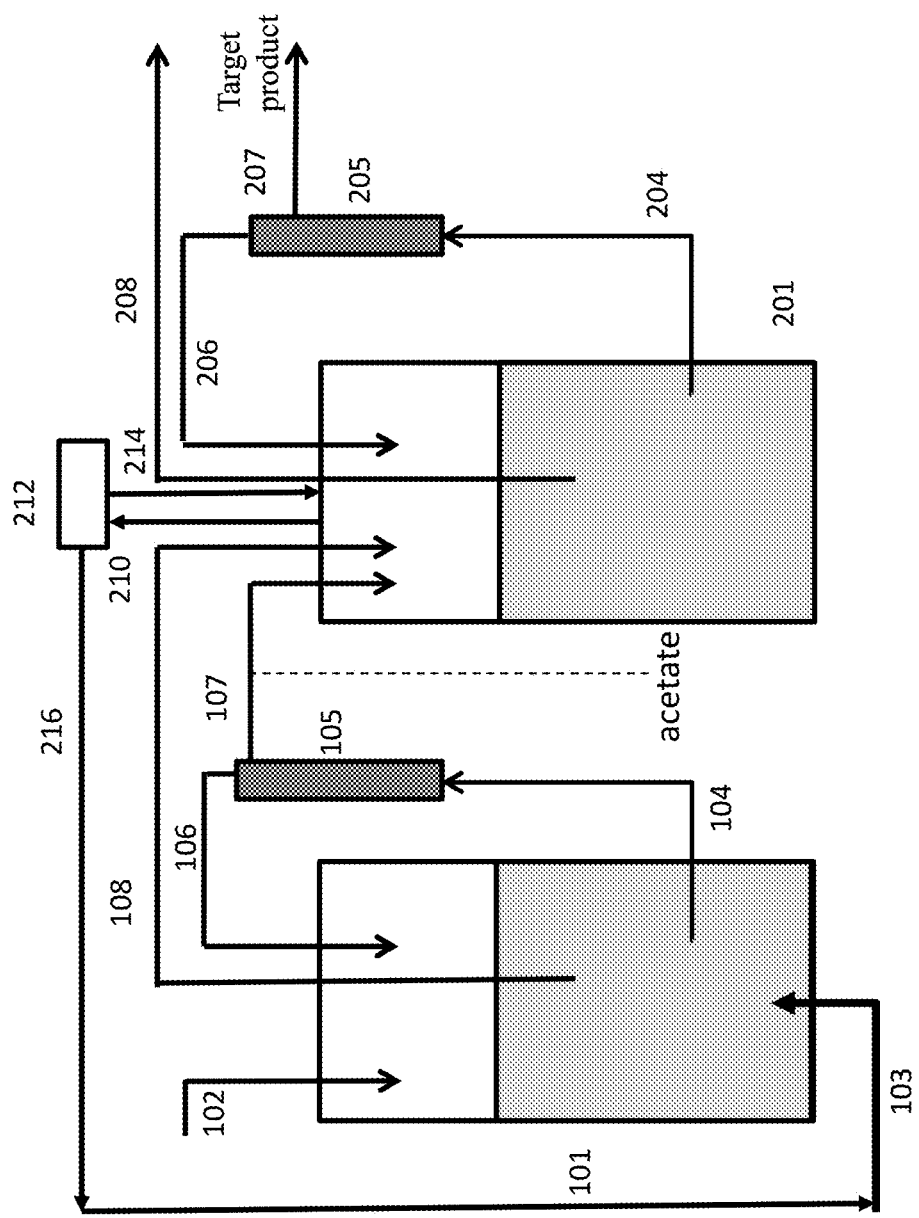
FIG. 1 is a diagram of an embodiment of the disclosure having a two-fermenter system for production of a target product from CO and optionally $H_2$, or $CO_2$ and $H_2$, wherein a $CO_2$ stream is recycled from the second bioreactor to the first bioreactor. Optionally, the $CO_2$ stream is treated to remove oxygen and form a substantially oxygen-free $CO_2$ stream.

The disclosure relates to the combination of a primary fermentation (first stage fermentation) that converts gas to acetate, with a secondary fermentation (second stage fermentation) that converts acetate to a target product.

Primary Fermentation

The primary fermentation uses a microorganism (the "primary microorganism") capable of converting gas to acetate. The primary fermentation may be a co-culture of two such organisms, which have similar or complementary growth requirements. Thus, the primary fermentation may involve a pure culture or a mixed culture.

The primary microorganism may, for example, be selected from *Acetobacterium, Acetoanaerobium, Alkalibaculum, Blautia, Butyribacterium, Clostridium, Desulfobacterium, Eubacterium, Methanosarcina, Moorella, Oxobacter, Peptostreptococcus, Pyrococcus Ruminococcus, Sporomusa*, and *Thermoanaerobacter*. In particular, the primary microorganism may be derived from a parental bacterium selected from *Acetobacterium woodii, Alkalibaculum bacchii, Blautia producta, Butyribacterium methylotrophicum, Carboxydothermus acetogenium, Clostridium aceticum, Clostridium autoethanogenum, Clostridium carboxidivorans, Clostridium coskatii, Clostridium drakei, Clostridium formicoaceticum, Clostridium ljungdahlii, Clostridium magnum, Clostridium ragsdalei, Clostridium scatologenes, Eubacterium limosum, Moorella thermoautotrophica, Moorella thermoacetica, Oxobacter pfennigii, Sporomusa ovata, Sporomusa silvacetica, Sporomusa sphaeroides*, and *Thermoanaerobacter kiuvi*. The primary microorganism may also be selected from *Acetitomaculum ruminis, Acetoanaerobium noterae, Acetobacterium bakii, Acetobacterium carbinolicum, Acetobacterium dehalogenans, Acetobacterium fimetarium, Acetobacterium malicum, Acetobacterium paludosum, Acetobacterium tundrae, Acetobacterium wieringae, Acetobacterium woodii, Acetohalobium arabicum, Acetonema longum, Blautia coccoides, Blautia hydrogenotrophica, Blautia producta, Blautia schinkii, Butyribacterium methylotrophicum, Clostridium aceticum, Clostridium autoethanogenum, Clostridium carboxidivorans, Clostridium drakei, Clostridium formicoaceticum, Clostridium glycolicum, Clostridium ljungdahlii, Clostridium magnum, Clostridium mayombei, Clostridium methoxybenzovorans, Clostridium ragsdalei, Clostridium scatologenes, Eubacterium aggregans, Eubacterium limosum, Moorella mulderi, Moorella thermoacetica, Moorella thermoautotrophica, Oxobacter pfennigii, Sporomusa acidovorans, Sporomusa aerivorans, Sporomusa malonica, Sporomusa ovata, Sporomusa paucivorans, Sporomusa rhizae, Sporomusa silvacetica, Sporomusa spaeroides, Spo-*

*romusa termitida*, *Thermoacetogenium phaeum*, *Thermoanaerobacter kivui*, *Acetobacterium*, *Moorella*, *Moorella* sp HUC22-1, *Moorella thermoacetica*, *Clostridium*, *Clostridium carboxidivorans*, *Clostridium drakei*, *Clostridium acidiurici*, *Pyrococcus*, *Pyrococcus furiosus*, *Eubacterium*, *Eubacterium limosum*, *Desulfobacterium*, *Cabroxydothermus*, *Acetogenium*, *Acetoanaerobium*, *Butyribaceterium*, *Butyribacterium methylotrophicum*, *Peptostreptococcus*, *Ruminococcus*, *Oxobacter*, *Oxobacter pfennigii*, *Methanosarcina*, *Carboxydothermus*, *Eubacterium limosum*, *Desulfotomaculum orientis*, *Peptococcus glycinophilus*, *Peptococcus magnets*, *Ignicoccus hospitalis*, *Thermoanaerobacter kivui*, and *Thermoacetogenium phaeum*. The microorganism may also be selected from those listed in Table 1 of Schiel-Bengelsdorf, FEBS Letters 586: 2191-2198, 2012.

In one embodiment, the primary microorganism is *Acetobacterium woodii*, *Clostridium autoethanogenum*, *Clostridium ljungdahlii*, or *Clostridium ragsdalei*.

In one embodiment, the primary microorganism is a Wood-Ljungdahl microorganism. "Wood-Ljungdahl" refers to the Wood-Ljungdahl pathway of carbon fixation as described, for example, by Ragsdale, *Biochim Biophys Acta*, 1784: 1873-1898, 2008. "Wood-Ljungdahl microorganisms" refers to microorganisms containing the Wood-Ljungdahl pathway, that is expresses the enzymes of the pathway. The primary microorganism often contains a native Wood-Ljungdahl pathway.

In one embodiment, the primary microorganism is an acetogen. "Acetogens" are obligately anaerobic bacteria that use the Wood-Ljungdahl pathway as their main mechanism for energy conservation and for synthesis of acetyl-CoA and acetyl-CoA-derived products, such as acetate (Ragsdale, Biochim Biophys Acta, 1784: 1873-1898, 2008). In particular, acetogens use the Wood-Ljungdahl pathway as a (1) mechanism for the reductive synthesis of acetyl-CoA from $CO_2$, (2) terminal electron-accepting, energy conserving process, (3) mechanism for the fixation (assimilation) of $CO_2$ in the synthesis of cell carbon (Drake, Acetogenic Prokaryotes, In: The Prokaryotes, 3rd edition, p. 354, New York, N.Y., 2006). All naturally occurring acetogens are C1-fixing, anaerobic, autotrophic, and non-methanotrophic.

The primary microorganism is capable of consuming a substrate (a "primary substrate") that provides carbon and/or energy. Typically, the primary substrate is gaseous and comprises a C1-carbon source, for example, CO, $CO_2$, and/or $CH_4$. In one embodiment, the primary substrate comprises a C1-carbon source of CO or CO+$CO_2$. The primary substrate may further comprise other non-carbon components, such as $H_2$, $N_2$, or electrons.

In one embodiment, the primary substrate comprises $CO_2$ and $H_2$. In another embodiment, the $H_2$ is renewable $H_2$. For example, the primary substrate may comprise about 1-80 or 1-30 mol % $CO_2$. In some embodiments, the primary substrate may comprise less than about 20, 15, 10, or 5 mol % $CO_2$. The primary substrate may comprise about 1, 2, 5, 10, 15, 20, or 30 mol % $H_2$. In some embodiments, the primary substrate may comprise a relatively high amount of $H_2$, such as about 60, 70, 80, or 90 mol % $H_2$. The primary substrate may also comprise some amount of CO and/or some amount of inert gases, such as $N_2$.

The primary substrate may be a waste gas obtained as a byproduct of an industrial process or from some other source, such as from automobile exhaust fumes or biomass gasification. In certain embodiments, the industrial process is selected from ferrous metal products manufacturing, such as a steel mill manufacturing, non-ferrous products manufacturing, petroleum refining, coal gasification, electric power production, carbon black production, ammonia production, methanol production, and coke manufacturing. In these embodiments, the substrate and/or C1-carbon source may be captured from the industrial process before it is emitted into the atmosphere, using any convenient method.

The primary substrate may be also syngas, such as syngas obtained by gasification of coal or refinery residues, gasification of biomass or lignocellulosic material, or reforming of natural gas. In another embodiment, the syngas may be obtained from the gasification of municipal solid waste or industrial solid waste.

The composition of the substrate may have a significant impact on the efficiency and/or cost of the reaction. For example, the presence of oxygen ($O_2$) may reduce the efficiency of an anaerobic fermentation process, and oftentimes the primary fermentation will be anaerobic. Depending on the composition of the substrate, it may be desirable to treat, scrub, or filter the substrate to remove any undesired impurities, such as toxins, undesired components, or dust particles, and/or increase the concentration of desirable components.

In certain embodiments a $CO_2$ electrolyzer may be used to generate at least a portion of the CO used as primary substrate and optionally a portion of any $O_2$ used in the secondary fermentation.

In certain embodiments, the primary fermentation is performed in the absence of carbohydrate substrates, such as sugar, starch, lignin, cellulose, or hemicellulose.

The primary fermentation produces at least one product (a "primary product"). Typically, this product will be acetate, although the primary fermentation may also produce additional products such as ethanol, lactate, and 2,3-butanediol. Microbial biomass, such as single cell protein, may also be considered a product, as it has potential applications in animal feed and fertilizers. Importantly, the terms "acetate" and "acetic acid" may be used interchangeably herein.

In some embodiments the primary fermentation may produce one or more of ethanol (WO 2007/117157), acetate (WO 2007/117157), 1-butanol (WO 2008/115080, WO 2012/053905, and WO 2017/066498), butyrate (WO 2008/115080), 2,3-butanediol (WO 2009/151342 and WO 2016/094334), lactate (WO 2011/112103), butene (WO 2012/024522), butadiene (WO 2012/024522), methyl ethyl ketone (2-butanone) (WO 2012/024522 and WO 2013/185123), ethylene (WO 2012/026833), acetone (WO 2012/115527), isopropanol (WO 2012/115527), lipids (WO 2013/036147), 3-hydroxypropionate (3-HP) (WO 2013/180581), terpenes, including isoprene (WO 2013/180584), fatty acids (WO 2013/191567), 2-butanol (WO 2013/185123), 1,2-propanediol (WO 2014/036152), 1-propanol (WO 2017/066498), 1-hexanol (WO 2017/066498), 1-octanol (WO 2017/066498), chorismate-derived products (WO 2016/191625), 3-hydroxybutyrate (WO 2017/066498), 1,3-butanediol (WO 2017/066498), 2-hydroxyisobutyrate or 2-hydroxyisobutyric acid (WO 2017/066498), isobutylene (WO 2017/066498), adipic acid (WO 2017/066498), 1,3-hexanediol (WO 2017/066498), 3-methyl-2-butanol (WO 2017/066498), 2-buten-1-ol (WO 2017/066498), isovalerate (WO 2017/066498), isoamyl alcohol (WO 2017/066498), and monoethylene glycol (WO 2019/126400).

Secondary Fermentation

The secondary fermentation uses a microorganism (the "secondary microorganism") capable of converting acetate to a product. The secondary fermentation may be a co-culture of two such organisms, which have similar or complementary growth requirements. Thus, the primary fermentation may involve a pure culture or a mixed culture. The secondary fermentation may be conducted as an anaerobic or aerobic process.

The secondary microorganism may be any microorganism capable of consuming acetate. The secondary microorganism may be a yeast or bacterial species. The secondary microorganism may be selected from those listed in the following table:

| Exemplar species | Used industrially | Typical fermentation type | Oxygenation | Known products |
|---|---|---|---|---|
| Escherichia coli | Yes | Batch | Any | Proteins, base chemicals, fine chemicals |
| Yarrowia lipolytica | Yes | Continuous | Aerobic | Bulk and fine [supplement] lipids |
| Saccharomyces cerevisiae | Yes | Batch | Anaerobic | Ethanol, dried distiller's grains and solubles |
| Saccharomyces cerevisiae | Yes | Batch | Aerobic | Biomass, proteins, Base Chemicals, fine chemicals |
| Geobacillus thermoglucosidasius | Yes | Batch | Aerobic | Enzymes [amylase] |
| Bacillus subtilis | Yes |  | Aerobic | Enzymes [decarboxylase, glucanase, hemicellulase, amylase, xylanse], bacteriocins, amino acids |
| Pseudomonas putida KT2440 | No | Batch | Aerobic | Proteins, base chemicals, fine chemicals |
| Cryptococcus curvatus | No | Continuous | Aerobic | Lipids |
| Rhodotorula glutinis | No | Continuous | Aerobic | Lipids |
| Lipomyces starkeyi | No | Continuous | Aerobic | Lipids |
| Cupriavidus necator/ Ralstonia eutropha/ Alicagenes eutrophus | No | Batch | Aerobic | Biomass, PHBs, PHAs, isobutanol |
| Clostridum kluyveri | Yes | Continuous | Anaerobic | Butanoate, hexanoate, octanoate, propionate |
| Methanosarcina acetivorans | Yes | Continuous | Anaerobic | Methane, biomass/digestate |
| Desulfonatronum cooperativum | No | Batch | Aerobic | N/A |
| Geoalkalibacter ferrihydriticus | No | Batch | Aerobic | N/A |
| Alkalispirillum mobile | No | Batch | Aerobic | N/A |
| Corynebacterium glutamicum | Yes | Batch | Aerobic | Amino acids, biomass, alcohols on research scale |

The secondary microorganism is capable of consuming a substrate (a "secondary substrate") that provides carbon and/or energy. Typically, the secondary substrate comprises the acetate produced by the primary fermentation. However, the secondary substrate may also contain additional sources of carbon and/or energy, such as sugar or starch. In specific embodiments, acetate provides at least 50%, at least 60%, at least 70%, at least 80%, at least 90%, at least 95%, or at least 99% of the carbon and/or energy requirements of the secondary microorganism. In some embodiments, however, acetate may be removed for another use and another substrate may drive the secondary fermentation.

The second fermentation produces at least one product, which may be referred to herein as a "target product." The target product may be an enzyme, such as alpha acetolactate decarboxylase, alpha amylase, catalase, chymosin, cyclodextrin glucanotransferase, beta glucanase, glucose isomerase, glucose oxidase, hemicellulase, lipase, maltogenic amylase, protease, pullulanase, xylanase, or cellulase. The target product may be a nutrient or additive, such as microbial biomass for example, single cell protein), amino acids (glutamate, lysine, threonine, phenylalanine, tryptophan, cysteine, valine, proline, arginine, histidine), lipids, or vitamins (B12, B2, biotin). The target product may be a chemical such as butanoate, hexanoate, octanoate, isobutanol, isoprene, or terpenes. The target product may also be, for example, methane, polyhydroxybutyrate, polyhydroxyalkanoate, 3-hydroxyproprionate, a $C_5$-$C_{20}$ alcohol, an organic acid, a ketone, a lipid, acetone, propanol, butanol, 2,3-butanediol, acetate, butyrate, caproate, propylene, butadiene, isobutylene, isobutyl acetate, succinate, mevalonate, itaconic acid, monellin, or ethylene. In some cases the target product may be just one or more of these products devoid of others, for example, devoid of lipids. In one embodiment, the target product may be polyhydroxybutyrate devoid of lipids. In another embodiment it may be polyhydroxyalkanoate devoid of lipids.

The secondary or target product may also be, for example, any of the products described and depicted by Lee, Nature Catalysis, 2: 18-33, 2019. The target product may be one or more of ethanol (WO 2007/117157), 1-butanol (WO 2008/115080, WO 2012/053905, and WO 2017/066498), butyrate (WO 2008/115080), 2,3-butanediol (WO 2009/151342 and WO 2016/094334), lactate (WO 2011/112103), butene (WO 2012/024522), butadiene (WO 2012/024522), methyl ethyl ketone (2-butanone) (WO 2012/024522 and WO 2013/185123), ethylene (WO 2012/026833), acetone (WO 2012/115527), isopropanol (WO 2012/115527), lipids (WO 2013/036147), 3-hydroxypropionate (3-HP) (WO 2013/180581), terpenes, including isoprene (WO 2013/180584), fatty acids (WO 2013/191567), 2-butanol (WO 2013/185123), 1,2-propanediol (WO 2014/036152), 1-propanol (WO 2017/066498), 1-hexanol (WO 2017/066498), 1-octanol (WO 2017/066498), chorismate-derived products (WO 2016/

191625), 3-hydroxybutyrate (WO 2017/066498), 1,3-butanediol (WO 2017/066498), 2-hydroxyisobutyrate or 2-hydroxyisobutyric acid (WO 2017/066498), isobutylene (WO 2017/066498), adipic acid (WO 2017/066498), 1,3-hexanediol (WO 2017/066498), 3-methyl-2-butanol (WO 2017/066498), 2-buten-1-ol (WO 2017/066498), isovalerate (WO 2017/066498), isoamyl alcohol (WO 2017/066498), and monoethylene glycol (WO 2019/126400).

Integrated Design

The primary and secondary fermentations may be integrated in some way, with each other and/or with upstream or downstream processes and or technologies.

One such integration integrates electrolysis with $O_2$ output. Both $CO_2$ electrolysis to produce CO, and water electrolysis to produce $H_2$, necessarily produce $O_2$ as a byproduct. In the context of two-stage fermentation, water electrolysis can be used to provide the $H_2$ in the $H_2+CO_2$ fermentation to make acetic acid occurring in the first stage fermentation. A large amount of $O_2$ may also be produced from the water electrolysis. The $O_2$ byproduct may not be pure and may not be an immediately saleable product. To sell the $O_2$ as industrial oxygen would require removal of trace gas components and moisture and would further require compression. However, the $O_2$ may be used in an aerobic fermentation, such as in the second stage fermentation, if it is an aerobic fermentation. Aerobic fermentation may be used to produce, for example: (1) cellulases by *Trichoderma reesei* or *Aspergillus niger*, as well as other species of filamentous fungi (growth on acetic acid on *A. niger* is documented, and co-consumption of glucose and acetic acid is documented on *T. reesei*) and (2) antibiotics (growth and production of penicillin is elevated when culture is provided acetic acid as well as glucose, pH 6.5).

If the second stage does not require oxygen or there is excess oxygen, the oxygen can be used for enhanced combustion in various refinery or steelmaking processes. The oxygen can also be used in gasification. Refinery burners with enhanced $O_2$ feed have greater efficiency (oxyfuel burners). Steel mills use waste gasses for heating cheaply for steel rolling or other processes, and as a basic oxygen furnace input.

Another integration involves the integration of nutrients between the primary and secondary fermentations. Excess vitamins, for example, B vitamins, could be transferred from stage 1 to stage 2. B vitamins help induce production of a broad range of hydrolytic enzymes in filamentous fungi. If the second stage fermentation uses yeast as a microorganism, yeast extract can provide carbon source and nutrients for growth. Yeast extract is also a nitrogen source (8 to 12 wt. % nitrogen) and can be a pH neutral source of N.

Another form of nutrient integration occurs when a particular nutrient that is required by both the first and second microorganisms for the first and second fermentations is added to the first nutrient medium in an amount that is sufficient for both fermentations. Thus, when the fermentation broth from the first bioreactor is transferred to the second bioreactor, one need not add that particular nutrient to the second bioreactor, or one need not add as much of the particular nutrient. Alternatively, the particular nutrient may not be required or utilized by the first microorganism and is merely present in the first fermentation without being utilized or consumed. In one embodiment, the first fermentation broth is transferred and utilized by the second fermentation's microorganism without the need to augment or alter its composition. Another aspect of nutrient integration involves recycling of the second fermentation broth back to the first fermenter so that remaining nutrients or products of the second fermentation can be utilized in the first fermentation. This aspect can be utilized in either the continuous culture or batch fed culture embodiments.

Another aspect of nutrient integration employs a nutrient in the first fermentation to induce or increase production of a product in the first fermentation that is useful for growth of the microorganism in the second fermentation and/or conversion by the microorganism in the second fermentation bioreactor. Thus, upon transfer of the first fermentation broth to the second bioreactor, the product in it stimulates biomass production in the second bioreactor or is fermented in the second bioreactor to form the first or a second target product.

In some embodiments of the disclosure, it is desirable that the first microorganism be removed from the first fermentation broth prior to transfer of the first fermentation broth to the second bioreactor. It may be desirable to recycle all or a portion of the first microorganism back to the first bioreactor. In other embodiments, the removed first microorganism may be used as biomass. Similarly, it may be desirable that the second microorganism be removed from the second fermentation broth prior to transfer of the second fermentation broth back to the first bioreactor. It may be desirable to use the removed second microorganism as biomass or to recycle the second microorganism back to the second bioreactor.

In one embodiment, the primary fermentation could be run at low pH, which could inhibit the growth of species from the secondary fermentation, if broth from the secondary fermentation were recycled back to the primary fermentation. This would also reduce acid compensation costs. The secondary fermentation could be run at a higher pH than the primary fermentation, ideally by more than 1 full pH unit. When acid is consumed in the first bioreactor, pH rises and so transfer of a higher pH second reactor fermentation broth to the first bioreactor reduces the amount of base, such as ammonia, that would need to be supplied to adjust the pH of the first bioreactor. Yeast, *E. coli*, and a wide range of microbes operate near pH 7 and can be used in the second bioreactor.

In another embodiment, an integration may be the recycling of tail gas from, for example, the secondary fermentation to the primary fermentation. The tail gas from one fermentation may contain $CO_2$ and/or $H_2$, which may be used as a substrate in the other fermentation. A challenge that may be faced with this integration occurs when the one of the bioreactors operates in an aerobic mode while the other operates in an anaerobic mode. For ease of understanding, this embodiment is explained wherein the primary fermentation is anaerobic and the secondary fermentation is aerobic. $O_2$ present in the tail gas from the secondary bioreactor must be separated and removed from the $CO_2$ containing tail gas stream before the tail gas is recycled to the primary bioreactor. The amount of $O_2$ removed should be enough so that any remaining $O_2$ that is passed to the primary bioreactor does not adversely affect the operations of the primary bioreactor beyond tolerances. Suitable techniques for separation include pressure swing adsorption (PSA), membrane separation, acid gas removal techniques, $CO_2$ solvents such as amine, methanol and the like for absorption using a solvent, cryogenic freezing out of $CO_2$, and scrubbing with a basic solution. The separation step may also involve the separation of nitrogen. The separation step may involve two or more separation stages in series or in parallel. The separation stages may be of the same technique or may employ different techniques. For example, two PSA units in series may be employed. In one embodiment, a first PSA may be used to remove $CO_2$ while a second PSA may be used to remove $O_2$ and reject $N_2$. Separated oxygen may be returned to the secondary bioreactor. Another way to remove $O_2$ from the gas to be recycled back to the first bioreactor is the use of yet a third fermenter that gets supplied with microbes from the second fermenter. This third fermenter will not be sparged with $O_2$ therefore putting the microbes in $O_2$ starvation mode. If the off-gas of the second bioreactor is led through this third vessel, the microbes will take all remaining $O_2$ out such that the gas leaving this third reactor can now be returned to the first bioreactor. The microbes in that third vessel will be transferred back (returned, recycled) to the second bioreactor. There will be a constant passage and return of microbes from the second bioreactor to that third fermentation vessel.

In another embodiment, the secondary fermentation could be run in batch mode, to allow for cleaning/sterilization between batches, while the primary fermentation could be run continuously. Whether operated in a continuous or batch mode, fermentation broth from the second fermenter may be recycled back to the primary fermentation. This recycling can be beneficial to make use of unconsumed nutrients that were present in the secondary fermentation thereby reducing overall operating and nutrient costs.

Fermentation and Separation

The term "fermentation" should be interpreted as a metabolic process that produces chemical changes in a substrate. For example, a fermentation process receives one or more substrates and produces one or more products through utilization of one or more microorganisms. The term "fermentation" should be interpreted as the process which receives one or more substrates and produces one or more products through the utilization of one or more microorganisms. Preferably the fermentation process includes the use of one or more bioreactors. The fermentation process may be described as either "batch" or "continuous". "Batch fermentation" is used to describe a fermentation process where the bioreactor is filled with raw material, for example the carbon source, along with microorganisms, where the products remain in the bioreactor until fermentation is completed. In a "batch" process, after fermentation is completed, the products are extracted, and the bioreactor is cleaned before the next "batch" is started. "Continuous fermentation" is used to describe a fermentation process in which the fermentation process is extended for longer periods of time, and product and/or metabolite is extracted during fermentation. Preferably the fermentation process is continuous.

Typically, the culture is performed in a bioreactor. The term "bioreactor" includes a culture/fermentation device consisting of one or more vessels, towers, or piping arrangements, such as a continuous stirred tank reactor (CSTR), immobilized cell reactor (ICR), trickle bed reactor (TBR), bubble column, gas lift fermenter, static mixer, or other vessel or other device suitable for gas-liquid contact. In some embodiments, the bioreactor may comprise a first growth reactor and a second culture/fermentation reactor. The substrate may be provided to one or both of these reactors. As used herein, the terms "culture" and "fermentation" are used interchangeably. These terms encompass both the growth phase and product biosynthesis phase of the culture/fermentation process.

The culture is generally maintained in an aqueous culture medium that contains nutrients, vitamins, and/or minerals sufficient to permit growth of the microorganism. Preferably the aqueous culture medium is a suitable microbial growth medium, such as a minimal microbial growth medium. Suitable media are well known in the art.

The culture/fermentation should desirably be carried out under appropriate conditions for production of the target product. Typically, the culture/fermentation is performed under anaerobic conditions. Reaction conditions to consider include pressure (or partial pressure), temperature, gas flow rate, liquid flow rate, media pH, media redox potential, agitation rate (if using a continuous stirred tank reactor), inoculum level, maximum gas substrate concentrations to ensure that gas in the liquid phase does not become limiting, and maximum product concentrations to avoid product inhibition. In particular, the rate of introduction of the substrate may be controlled to ensure that the concentration of gas in the liquid phase does not become limiting, since products may be consumed by the culture under gas-limited conditions.

Target products may be separated or purified from a fermentation broth using any method or combination of methods known in the art, including, for example, fractional distillation, evaporation, pervaporation, gas stripping, phase separation, and extractive fermentation, including for example, liquid-liquid extraction. In certain embodiments, target products are recovered from the fermentation broth by continuously removing a portion of the broth from the bioreactor, separating microbial cells from the broth (conveniently by filtration), and recovering one or more target products from the broth. Alcohols and/or acetone may be recovered, for example, by distillation. Acids may be recovered, for example, by adsorption on activated charcoal. Separated microbial cells are preferably recycled back to the bioreactor. The cell-free permeate remaining after target products have been removed is also preferably returned to the bioreactor. Additional nutrients may be added to the cell-free permeate to replenish the medium before it is returned to the bioreactor.

In embodiment of the disclosure, prior to transferring first fermentation broth to the second bioreactor, a product of the first fermentation is removed from the first fermentation broth. The product removed may be some or all of the acetate. The product removed may be a secondary product of the fermentation process. Alternatively, a secondary product of the first fermentation process may be removed and recovered (or discarded) only after the second fermentation. So long as the secondary product is not further converted by the second microorganism and does not negatively affect the second fermentation, it need not be removed until after the second fermentation.

The methods and systems of the disclosure are herein described with reference to the Figures. FIG. 1 demonstrates a two-stage system to produce target product(s) from a gaseous stream comprising CO and $H_2$, or $CO_2$ and $H_2$. The system provides a primary bioreactor 101 having a media inlet 102, a gas inlet port 103, a separator means 104, a permeate stream outlet 107, and a bleed stream outlet 108. The primary bioreactor is connected to a secondary bioreactor 201, having a separator 205, a permeate stream outlet 207 and a bleed stream outlet 208.

In use, the primary bioreactor 101 may contain fermentation broth comprising a culture of one or more acetogenic bacteria in a liquid nutrient medium. Medium is added to the bioreactor 101 in a continuous or semi-continuous manner throughout the media inlet 102. A gaseous substrate is supplied to the bioreactor 101 via the gas inlet port 103. The separator means is adapted to receive at least a portion of broth from the bioreactor 101 via a first output conduit 104 and pass it through the separator 105 configured to substantially separate the microorganism cells (the retentate) from the rest of the fermentation broth (the permeate). At least a portion of the retentate is returned to the first bioreactor via a first return conduit 106, which ensures that the broth culture density is maintained at an optimal level. The separator 105 is adapted to pass at least a portion of the permeate out of the bioreactor 101 via a permeate delivery conduit 107. The permeate delivery conduit 107 feeds the cell free permeate to the secondary bioreactor 201. In certain embodiments of the disclosure, at least a portion of the cell free permeate is removed for product extraction and/or at least a portion of the cell free permeate is recycled to primary bioreactor with the remainder of the cell free permeate stream being fed to the secondary bioreactor 201. A broth bleed output 108 is provided to directly feed broth from the primary bioreactor 101 to the secondary bioreactor 202. In certain embodiments the broth bleed and permeate are combined prior to being fed to the secondary bioreactor.

Secondary bioreactor 201 contains a culture of one more microorganisms in a liquid nutrient medium. An aerobic microorganism, such as yeast or *E. coli*, are used as specific examples, but any suitable microorganism may be employed in secondary bioreactor 201. Secondary bioreactor 201 receives broth and/or permeate from primary bioreactor 101 in a continuous or semi-continuous manner through broth bleed output 108 and permeate delivery conduit 107. The separator 205 is adapted to receive at least a portion of broth from secondary bioreactor 201 via a first output conduit 204. Separator 205 is configured to substantially separate the microorganism cells (the retentate) from the rest of the fermentation broth (the permeate). At least a portion of the retentate is returned to secondary bioreactor 201 via a second return conduit 206, which ensures that the broth culture density in secondary bioreactor 201 is maintained at an optimal level. Separator 205 is adapted to pass at least a portion of the permeate out of secondary bioreactor 201 via a permeate removal conduit 207. Broth bleed output 208 is provided directly to remove broth from secondary bioreactor 201. Broth bleed output 208 may be treated to remove the biomass for target product extraction using known methods. The substantially biomass free bleed stream and the permeate streams may be combined to produce a combined stream. In certain embodiments of the disclosure, the combined stream can be returned to the primary reactor to supplement the liquid nutrient medium being continuously added. In certain embodiments, it may be desirable to further process the recycle stream to remove undesired or desired by-products of the secondary fermentation. In certain embodiments, the pH of the recycle stream may be adjusted, and further vitamins and/or metals added to supplement the stream.

Tail gas stream 210 from secondary bioreactor 201 is passed to oxygen removal unit 212 to generate a substantially oxygen free $CO_2$ stream. Oxygen removal unit may be, for example, one or more PSA units, membrane separation units, scrubbers, absorption using solvent(s), or any combination thereof. Substantially oxygen free $CO_2$ stream is passed in line 216 and recycled to primary bioreactor 101 through inlet gas port 103. Substantially oxygen free means the stream comprises less than about 1 mol-percent O2, less than about 500 mol-ppm $O_2$ or less than about 100 mol-ppm $O_2$. $O_2$ that is removed from the tail gas 210 in oxygen removal unit 212 may be recycled to the secondary bioreactor 201 through line 214.

Figure 2:
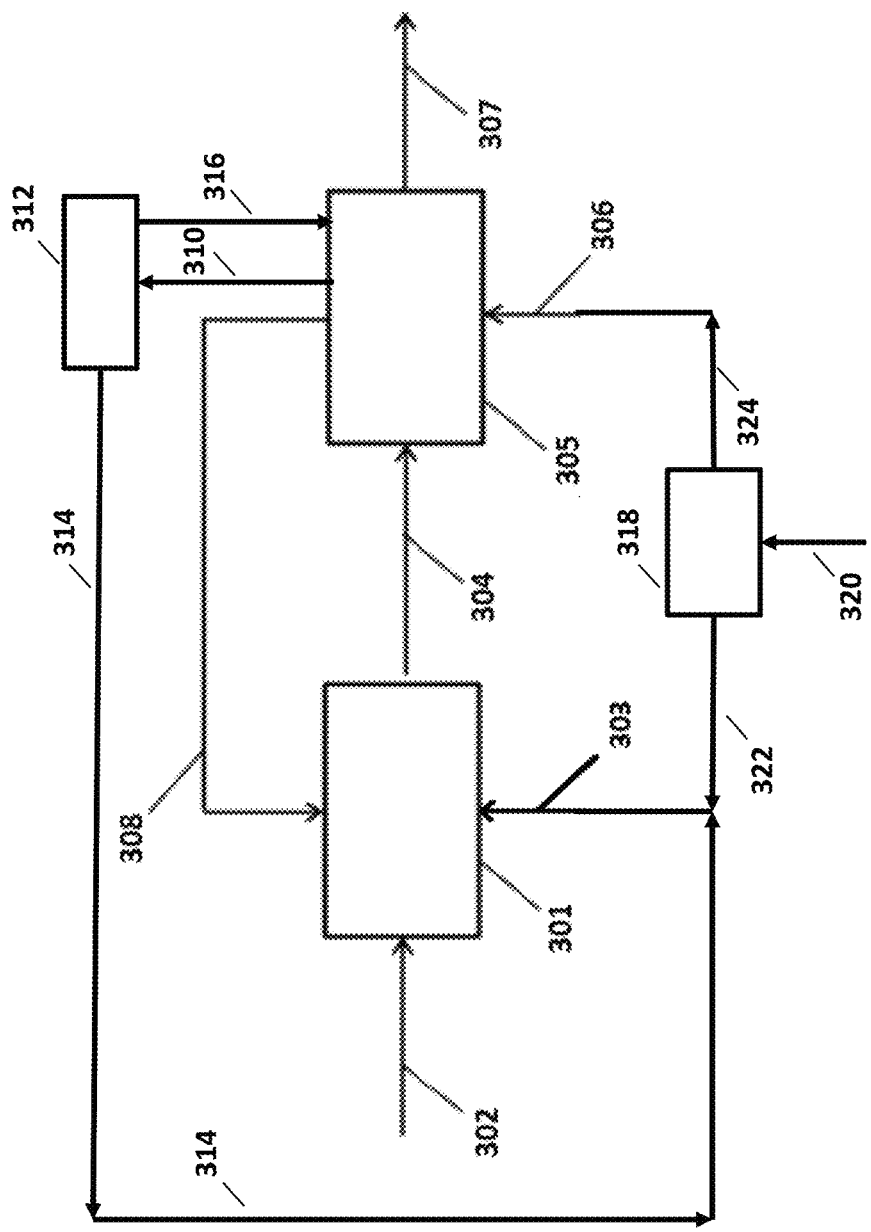
FIG. 2 is a diagram of an embodiment of the disclosure having a two-fermenter system for production of a target product from CO and optionally $H_2$, or $CO_2$ and $H_2$, wherein a $CO_2$ stream is recycled from the second bioreactor to the primary bioreactor. Optionally, the $CO_2$ stream can be treated to remove oxygen and form a substantially oxygen-free $CO_2$ stream prior to its recycling to the primary bioreactor. Additionally.

FIG. 2 demonstrates a simplified system for the production of target product(s) from a gaseous stream comprising CO and $H_2$, or $CO_2$ and $H_2$, wherein the substantially acetate-free media is recycled from the secondary bioreactor to the primary bioreactor. The system includes a primary anaerobic bioreactor 301 having a media inlet 302, a gas inlet port 303, an acetate-containing treated bleed stream 304, a secondary aerobic bioreactor 305, an oxygen source 306, a target product and biomass-containing product stream 307, and an acetate-depleted recycled media stream. In one embodiment, the gaseous stream is produced by an electrolyzer.

In use, the primary bioreactor 301 contains fermentation broth comprising a culture of one or more acetogenic bacteria in a liquid nutrient medium. Medium is added to primary bioreactor 301 through the media inlet 302. A gaseous substrate comprising either CO and optionally $H_2$, or $CO_2$ and $H_2$, or mixtures thereof, is supplied to the primary bioreactor 301 via a gas inlet port 303, wherein the gas is converted by the bacteria to acetate. The primary bioreactor 301 is maintained at a pH in the range of 2.5-5, or 3-4, or 6.5-7, with pH optionally partially controlled by the addition of base as necessary. The acetate product leaves the primary bioreactor in an aqueous broth stream, which is treated to remove the biomass using known methods. The resulting acetate-containing treated bleed stream 304 is fed to a secondary aerobic bioreactor 305. In the secondary bioreactor 305, acetate in the treated bleed stream is converted to target products and biomass by a microorganism, such as for example a microorganisms. Oxygen is supplied to the aerobic fermentation by an oxygen or air inlet port 306. The target product-containing microorganism cells are removed from the secondary bioreactor 305 by filtration, resulting in a target product- and biomass-containing product stream 307 and a permeate stream 308. Because the aerobic fermentation consumes acetate, the pH of the broth increases as acetic acid is consumed, and the pH of the permeate stream 308 is consequently nominally higher than the pH of the acetate-containing broth stream 304. The dilution rate of the secondary bioreactor 305 is maintained such that the pH of the permeate stream 308 remains in the range of, for example, 5-7; or 7.0-7.5; or 7.5-9; or 10-11. The acetate-depleted permeate stream 308 is returned to the primary bioreactor 301. In addition to recycling a substantial portion of the water, salts, metals, and other nutrients that make up the media of the primary bioreactor 301, the recycled permeate stream 308 acts to reduce significantly the cost of fermentation pH control relative to a system in which pH is controlled only by direct addition of base to the bioreactor media.

Tail gas generated in secondary bioreactor 305 is removed in tail gas line 310 and conducted to oxygen separation unit 312. Oxygen separation unit may be, for example, one or more PSA units, membrane separation units, scrubbers, absorption using solvent(s), or any combination thereof. At least oxygen is removed from the tail gas in the oxygen separation unit. The resulting $CO_2$ stream that is substantially free of $O_2$ is then conducted in line 314 to gas inlet port 303 and introduced into primary bioreactor 301. $O_2$ removed in the oxygen separation unit may be recycled to secondary bioreactor 305 through line 316. FIG. 2 further illustrates the embodiment employing the optional water 2rolyzer. Water stream 320 is introduced into electrolyzer 318 where a $H_2$ stream is generated by electrolysis and the $H_2$ stream is conducted in line 322 to gas inlet port 303 and introduced into primary bioreactor 301 along with the gaseous substrate discussed above. Similarly, electrolyzer 318 generates an $O_2$ stream, which is conducted in line 324 to inlet port 306 of secondary bioreactor 305.

All references, including publications, patent applications, and patents, cited herein are hereby incorporated by reference to the same extent as if each reference were individually and specifically indicated to be incorporated by reference and were set forth in its entirety herein. The reference to any prior art in this specification is not, and should not be taken as, an acknowledgement that that prior art forms part of the common general knowledge in the field of endeavor in any country.

The use of the terms "a" and "an" and "the" and similar referents in the context of describing the disclosure (especially in the context of the following claims) are to be construed to cover both the singular and the plural, unless otherwise indicated herein or clearly contradicted by context. The terms "comprising," "having," "including," and "containing" are to be construed as open-ended terms (that is, meaning "including, but not limited to") unless otherwise noted. The term "consisting essentially of" limits the scope of a composition, process, or method to the specified materials or steps, or to those that do not materially affect the basic and novel characteristics of the composition, process, or method. The use of the alternative (for example, "or") should be understood to mean either one, both, or any combination thereof of the alternatives. As used herein, the term "about" means±20% of the indicated range, value, or structure, unless otherwise indicated.

"A portion of" may refer to a volume or weight portion of a composition such as a fermentation broth or tail gas created in a fermentation process. The term may also refer to a subset of components of a composition, such as when a fermentation broth or tail gas has been subjected to a purification process to remove components—whether wanted or unwanted. Thus, if a composition comprises a mixture of components, the portion may comprise the same mixture of components, an altered ratio of components, or an altered set of components. "At least a portion" may include the entirety or all of a composition.

Recitation of ranges of values herein are merely intended to serve as a shorthand method of referring individually to each separate value falling within the range, unless otherwise indicated herein, and each separate value is incorporated into the specification as if it were individually recited herein. For example, any concentration range, percentage range, ratio range, integer range, size range, or thickness range is to be understood to include the value of any integer within the recited range and, when appropriate, fractions thereof (such as one tenth and one hundredth of an integer), unless otherwise indicated.

All methods described herein can be performed in any suitable order unless otherwise indicated herein or otherwise clearly contradicted by context. The use of any and all examples, or exemplary language (for example, "such as") provided herein, is intended merely to better illuminate the disclosure and does not pose a limitation on the scope of the invention unless otherwise claimed. No language in the specification should be construed as indicating any non-claimed element as essential to the practice of the disclosure.

Specific embodiments of this disclosure are described herein. Variations of those specific embodiments may become apparent to those of ordinary skill in the art upon reading the foregoing description. The inventors expect skilled artisans to employ such variations as appropriate, and the inventors intend for the disclosure to be practiced otherwise than as specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

The invention claimed is:

1. A method for producing at least one target product from carbon monoxide (CO) and optionally hydrogen ($H_2$), or from carbon dioxide ($CO_2$) and $H_2$, the method comprising:
   (i) introducing a gaseous substrate comprising at least CO and optionally $H_2$, or at least $CO_2$ and $H_2$ into a first bioreactor containing a culture of at least one first microorganism in a first liquid nutrient medium and anaerobically fermenting the gaseous substrate to produce at least one first product selected from the group consisting of ethanol, lactate, and 2,3-butanediol in a first fermentation broth, wherein the first microorganism is a Wood-Ljungdahl microorganism; and
   (ii) transferring at least a portion of the first fermentation broth to a second bioreactor containing a culture of at least one second microorganism in a second liquid nutrient medium, wherein the second microorganism is a different species from the first microorganism, and aerobically fermenting the first product to produce at least a first target product in a second fermentation broth; wherein the at least one second microorganism is selected from the group consisting of yeasts, *Escherichia coli, Geobacillus thermoglucosidasius, Pseudomonas putida* KT2440, *Cupriavidus necator/Ralstonia eutropha/Alcaligenes eutrophus, Desulfonatronum cooperativum, Geoalkalibacter ferrihydriticus, Alkalispirillum mobile*, and *Corynebacterium glutamicum*;
   wherein the first target product is not a lipid.

2. The method of claim 1, wherein the first liquid nutrient medium comprises a nutrient that is utilized by the second microorganism but not by the first microorganism.

3. The method of claim 1, wherein the second liquid nutrient medium is the first fermentation broth.

4. The method of claim 1, wherein the second fermentation broth is transferred back to the first bioreactor.

5. The method of claim 1, wherein the first target product is selected from the group consisting of an alcohol, an organic acid, and a ketone.

6. The method of claim 1, wherein prior to transferring at least a portion of the first fermentation broth to the second bioreactor, at least one first product is removed from the first fermentation broth.

7. The method of claim 1, wherein after fermentation in the second bioreactor, at least one first product produced in the first bioreactor is separated from the second fermentation broth.

8. The method of claim 1, wherein the culture in the first, second, or first and second bioreactor comprises a co-culture.

9. The method of claim 5, wherein the first target product is one or more selected from the group consisting of ethanol, acetone, propanol, butanol, 2,3-butanediol, acetate, butyrate, propionate, caproate, butadiene, isobutyl acetate, polyhydroxyalkanoates, succinate, mevalonate, itaconic acid, and monellin.

10. The method of claim 1, further comprising the steps of:
   (i) obtaining a tail gas comprising at least $CO_2$ and $O_2$ from the second bioreactor;
   (ii) removing at least a portion of the $O_2$ from the tail gas to form an $O_2$-depleted tail gas; and
   (iii) recycling at least a portion of the $O_2$-depleted tail gas to the first bioreactor.

11. The method of claim 10, wherein the removing of at least a portion of the $O_2$ from the tail gas is accomplished using one or more stages of pressure swing adsorption, membrane separation, scrubbing with a basic solution, absorption using a solvent, or any combination thereof.

12. The method of claim 10, further comprising recycling the $O_2$ from the removing of at least a portion of the $O_2$ from the tail gas to the second bioreactor.

13. The method of claim 1, wherein the Wood-Ljungdahl microorganism in the first bioreactor is selected from the group consisting of *Acetobacterium, Moorella, Clostridium, Pyrococcus, Eubacterium, Desulfobacterium, Carboxydothermus Acetogenium, Acetoanaerobium, Butyribacterium, Peptostreptococcus, Ruminococcus*, and *Oxobacter*.

14. The method of claim 1, wherein the Wood-Ljungdahl microorganism in the first bioreactor is *Acetobacterium woodii*.

15. The method of claim 1, wherein the Wood-Ljungdahl microorganism in the first bioreactor is selected from the group consisting of *Clostridium autoethanogenum, Clostridium ljungdahlii*, and *Clostridium ragsdalei*.

16. The method of claim 1, wherein a nutrient is added to the first liquid nutrient medium to increase production of a second product in the first fermentation broth, wherein the second product is transferred in the portion of the first fermentation broth to the second bioreactor and stimulates biomass production in the second bioreactor or is fermented in the second bioreactor to form the first or a second target product.

17. The method of claim 1, further comprising recovering a gaseous stream comprising CO and optionally $H_2$, or $CO_2$ and $H_2$ from the first bioreactor and recycling the gaseous stream to the first bioreactor.

18. The method of claim 1, further comprising recycling at least a portion of the second fermentation broth to the first bioreactor.

19. The method of claim 1, further comprising removing the first microorganism from the first fermentation broth before passing at least a portion of the first fermentation broth to the second bioreactor and recycling the first microorganism to the first bioreactor.

20. The method of claim 1, further comprising removing the second microorganism from the second fermentation broth and recycling the second microorganism to the second bioreactor.

21. The method of claim 1, further comprising using an electrolyzer to generate at least a portion of the $H_2$ in the gaseous substrate and/or at least a portion of 02 introduced into the second bioreactor.

22. The method of claim 1, wherein the second microorganism is a yeast.

23. The method of claim 1, wherein the second microorganism is *Escherichia coli*.

24. The method of claim 1, wherein the culture in the second bioreactor comprises a co-culture.

25. The method of claim 1, wherein the second fermentation broth is more than 1 full pH unit higher than the pH in the first fermentation broth.

26. The method of claim 1, wherein the first target product is at least one selected from the group consisting of propylene, isobutylene, and ethylene.

* * * * *